United States Patent [19]

Mantel

[11] 4,056,618

[45] Nov. 1, 1977

[54] NOVEL DIURETIC AND ANTIHYPERTENSIVE COMPOSITION

[75] Inventor: Olivier Mantel, Montmorency, France

[73] Assignee: Roussel-Uclaf, Paris, France

[21] Appl. No.: 674,755

[22] Filed: Apr. 8, 1976

[30] Foreign Application Priority Data

Apr. 11, 1975 France .................. 75.11377

[51] Int. Cl.² .................. A61K 31/535; A61K 31/505
[52] U.S. Cl. .................. 424/246; 424/251
[58] Field of Search .................. 424/246, 251

[56] References Cited

U.S. PATENT DOCUMENTS 3,275,625  9/1966  Muller et al. .................. 260/243 D

OTHER PUBLICATIONS

Antlitz et al. —Chem. Abst., vol. 67 (1967), p. 31442h.
Verrient —Chem. Abst., vol. 66 (1967), p. 9888y.

Primary Examiner—Sam Rosen
Attorney, Agent, or Firm—Hammond & Littell

[57] ABSTRACT

Novel diuretic and antihypertensive compositions comprising an effective amount of triamterene or 2,4,6-triamino-6-phenylpteridine having the formula

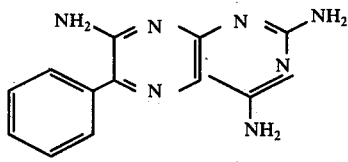

and an effective amount of cyclothiazide or the 1,1-dioxide of 6-chloro-3,4-dihydro-3-(2-norbornen-5-yl)-2H-1,2,4-benzothiadiazine-7-sulfonamide having the formula

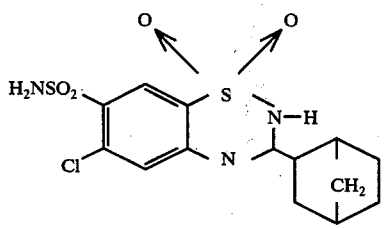

and a method of inducing diuresis and antihypertensive activity in warm-blooded animals.

7 Claims, No Drawings

NOVEL DIURETIC AND ANTIHYPERTENSIVE COMPOSITION

STATE OF THE ART

French BSM Patent No. M 1014 describes the use of triamterene as a diuretic and antihypertensive agent and French BSM Patent No. M 1367 describes cyclothiazide as a diuretic and antihypertensive agent and the two products have been used in human therapy for a number of years. It is also known to mix derivatives of the triamterene type and of the thiazide type. A mixture of triamterene and benzothiazide is sold in France under the name Diteriam as a diuretic and antihypertensive.

OBJECT OF THE INVENTION

It is an object of the invention to provide improved diuretic and antihypertensive compositions.

It is another object of the invention to provide a novel process of inducing diuresis and antihypertensive activity in warm-blooded animals, including humans.

These and other objects and advantages of the invention will become obvious from the following detailed description.

THE INVENTION

The novel diuretic and antihypertensive compositions of the invention are comprised of an effective amount of triamterene and cyclothiazide with the optional presence of an inert pharmaceutical carrier. The compositions have the desired diuretic and antihypertensive properties of the 2 components but have unexpected properties.

Cyclothiazide is a salidiuretic of strong and prolonged action which causes a continued and regular electrolyte emission without being violent. When used alone, as the other salidiuretics, it causes a hypokaliemia which is a cause of fatigue and diverse troubles.

Triamterene is a diuretic that increases natriuresis and aqueous diuresis but reduces kaliuresis and because of this antikaliuresis effect, triamterene counter balances the kaliuresis effect of cyclothiazide. This permits the therapeutic use of the compositions of the invention for a diuretic and antihypertensive efficient treatment for a prolonged duration while maintaining a satisfactory water-electrolyte equilibrium in the blood during the treatment.

In the compositions of the invention, the mixture may contain 10 to 200 parts, preferably 25 to 75 parts, by weight of triamterene per one part by weight of cyclothiazide and most preferred is a ratio of 50 parts by weight of triamterene per one part by weight of cyclothiazide. The activity was particularly remarkable and unexpected in the sense that while assuring very important natriuresis and aqueous diuretic effect, the compositions permit a very precious economy of potassium thanks to a urinary elimination reduced to a physiological level so one is able to ascertain a beneficial effect with this mixture.

This activity is also interesting to the same extent as the observed toxicity of the mixture was less than that one would expect from the toxicity of one of the components. In effect, when administered orally to mice, the composition of the invention has a lower toxicity than the toxicity of an equal amount of triamterene while cyclothiazide is not toxic. This is a supplemental and unexpected advantage of the compositions of the invention.

The compositions of the invention are useful in human therapy for the treatment of edematosis or sodium-water retension syndromes, cardiac insufficiency, of pregnant toxemia (beginning in the 4th month), of certain obesities, of cirrhosis, in the treatment of severe and resistant edemas, particularly that of congestive cardiac insufficiency and in the prolonged treatment of arterial hypertension.

The compositions may be in the form of tablets, dragees, gelules, granules, drinkable suspensions, suppositories or injectable solutions or suspensions prepared in the usual manner. The excipient or inert pharmaceutical carrier may be those well known in the art such as talc, colloidal silica, arabic gum, lactose, starch, magnesium stearate, cacao butter, aqueous or non-aqueous vehicles, fatty bodies of animal or vegetable origin, paraffinic derivatives, glycols, preservatives and/or diverse wetting agents, dispersants or emulsifiers.

The novel method of the invention for inducing diuresis and antihypertensive activity in warm-blooded animals, including humans, comprises administering to warm-blooded animals a diuretic and antihypertensively effective amount of a mixture of triamterene and cyclothiazide. The composition may be administered orally, rectally or parenterally and may be administered orally at a dose of 2 to 15 mg/kg.

In the following examples there are described several preferred embodiments to illustrate the invention. However, it should be understood that the invention is not intended to be limited to the specific embodiments.

EXAMPLE 1

Tablets were prepared consisting of 150 mg of triamterene, 3 mg of cyclothiazide and sufficient excipient comprised of aerosil, corn starch, treated starch, lactose, talc and magnesium stearate to obtain a tablet weighing 350 mg.

EXAMPLE 2

Gelules were prepared consisting of 200 mg of triamterene, 4 mg of cyclothiazide and sufficient excipient comprised of talc, magnesium stearate and aerosil to obtain a final weight of 500 mg.

PHARMACOLOGICAL DATA

A. Diuretic Activity

The diuretic activity was determined for cyclothiazide and triamterene and mixtures thereof on aqueous diuresis, sodium uresis and potassium uresis in normal rats subjected to a hydrosaline surcharge. Male rats of Sprague Dawley SPF (Specific Pathogen Free) strain weighing 180 to 200 g were not fed for 17 hours ($h$-18) before treatment and were placed on an aqueous diet one hour ($h$-2) before treatment. Groups of 10 rats were used for each product and 10 rats were used as controls and each rat received orally at the start of the treatment ($h$-1) a suspension of the product in a 0.25% aqueous solution of carboxymethylcellulose or only the aqueous solution in a volume of 0.5 ml/100 g of body weight. One hour later ($h$-0), the rats received intraperitoneally a hydrosaline surcharge (aqueous solution of sodium chloride at 9 p 1000) at a rate of 5 ml/100 g of body weight and then were placed in pairs in metabolism cages.

The urine was obtained over 4 hours (forced urination at the beginning before being placed in the cages and at the end of the test) and the volume of the urine was measured. After rinsing the collected material with distilled water, the sodium and potassium were determined by flame photometry. The doses used were 0.2 mg/kg of cyclothiazide, 10 mg/kg of triamterene and a mixture of 0.2 mg/kg of cyclothiazide and 10 mg/kg of triamterene and the results are reported in Table I.

TABLE I

| Products Administration in mg/kg | Urine excretion over 4 hours | | | | | | | |
|---|---|---|---|---|---|---|---|---|
| | Volume | | Na | | K | | | |
| | ml/rat | Variation in % controls | mg/rat | Variation in % controls | mg/rat | Variation in % controls | Ratio of Na/K |
| Controls | 1,8 ± 0,3 | | 6,6 ± 0,7 | | 5,1 ± 0,3 | | 1,3 ± 0,1 |
| Cyclothiazine - 0.2 | 3,2 ± 0,3 | + 78 | 15,7 ± 1,0 | + 138 | 7,3 ± 0,6 | + 43 | 2,3 ± 0,2 |
| Triamterene - 10 | 4,8 ± 0,4 | + 166 | 20,3 ± 1,3 | + 208 | 3,2 ± 0,5 | − 37 | 7,6 ± 1,2 |
| Combination of 0.2 of Cyclothiazide and 10 of Triamterene | 6,2 ± 0,4 | + 244 | 24,1 ± 1,0 | + 265 | 3,0 ± 0,3 | − 41 | 8,8 ± 0,8 |

The data in Table I shows that the composition of the invention from the level of diuresis and natriuresis possesses the excellent efficacy of each of its components but it also is entirely remarkable that this diuresis and natriuresis is accompanied by a great reduction in the potassium elimination because this elimination is, in an unexpected manner, much inferior to that one would have expected from the properties of the components of the mixture.

B. Acute Toxicity

The acute toxicity was determined on groups of 10 female swiss mice weighing about 20 g and the products were orally administered in aqueous suspension with an esophagus probe. The compositions tested were cyclothiazide alone, and triamterene alone and a mixture at a rate of 1 part of cyclothiazide of 50 parts of triamterene. The results are in Table II.

TABLE II

| Product | $DL_{50}$ in mg/kg |
|---|---|
| cyclothiazide | no mortality at 6000 |
| triamterene | 285 |
| cyclothiazide + triamterene | 440 of triamterene + 8.8 of cyclothiazide |

The toxicity is less for the mixture of cyclothiazide and triamterene than for triamterene alone which means that the mixture of cyclothiazide with triamterene causes a clear lessening of the toxicity of the latter product.

Various modifications of the composition and method of the invention may be made without departing from the spirit or scope thereof and it should be understood that the invention is to be limited only as defined in the appended claims.

I claim:

1. A diuretic and antihypertensive composition comprising an antihypertensively and diuretically effective amount of triamterene and cyclothiazide in a weight ratio of 10 to 200 parts of triamterene to one part of cyclothiazide with the optional presence of an inert pharmaceutical carrier.

2. The composition of claim 1 wherein the weight ratio of triamterene to cyclothiazide is 25 to 1 to 75 to 1.

3. The composition of claim 1 wherein the weight ratio of triamterene to cyclothiazide is 50 to 1.

4. The method of inducing diuresis and antihypertensive activity in warm-blooded animals comprising administering to warm-blooded animals a diuretic and antihypertensively effective amount of a composition of claim 1.

5. The method of claim 4 where the composition is orally administered.

6. The method of claim 4 wherein the weight ratio of triamterene to cyclothiazide is 25 to 1 to 75 to 1.

7. The method of claim 4 wherein the triamterene-cyclothiazide weight ratio is 50 to 1.

* * * * *